US00PP34450P2

(12) United States Plant Patent
Kleinwee

(10) Patent No.: US PP34,450 P2
(45) Date of Patent: Jul. 26, 2022

(54) ***PETUNIA* PLANT NAMED 'PEHY0059'**

(50) Latin Name: *Petunia hybrida*
Varietal Denomination: 'PEHY0059'

(71) Applicant: SYNGENTA CROP PROTECTION AG, Basel (CH)

(72) Inventor: Theodorus Cornelis Maria Van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/546,218

(22) Filed: Dec. 9, 2021

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824
See application file for complete search history.

(56) References Cited

PUBLICATIONS

CPVO hit on UPOV QZ PBR 2021/1877 on a *Petunia* plant named, 'PEHY0059', filed Jul. 16, 2021.*

* cited by examiner

*Primary Examiner* — Anne Marie Grunberg
(74) *Attorney, Agent, or Firm* — Dale Skalla

(57) ABSTRACT

A new *Petunia* plant named 'PEHY0059' particularly distinguished by its medium to small sized, light yellow flowers with red eye that changes color when aging, medium early flowering and a mounding to semi trailing plant habit.

1 Drawing Sheet

Latin name of the genus and species of the plant claimed: *Petunia hybrida.*

Varietal denomination: 'PEHY0059'.

BACKGROUND OF THE NEW PLANT

The present invention comprises a new *Petunia*, botanically known as *Petunia hybrida*, and hereinafter referred to by the variety name 'PEHY0059'.

'PEHY0059' is a product of a planned breeding program. The new cultivar has medium to small sized, light yellow flowers with red eye, that changes color when aging, medium early flowering and a mounding to semi trailing plant habit.

'PEHY0059' originated from a hybridization made in October 2017 in a controlled breeding environment in Enkhuizen, The Netherlands. The female parent was the proprietary selection 'PETBC0636-2V' (not patented in US). Compared to 'PEHY0059', it has a bit more trailing plant habit, a smaller flower, is later flowering and has a burgundy-red flower color with yellow stripes.

The male parent of 'PEHY0059' was the unpatented proprietary selection 'BB1214-1V' (not patented); a plant with somewhat bigger flowers, a bit more upright plant habit, and a yellow flower color with blue eye.

The resulting seeds were sown in January 2018. 'PEHY0059' was selected as one flowering plant within the progeny of the stated cross in May 2018 in a controlled environment in Enkhuizen, The Netherlands.

The first act of asexual reproduction of 'PEHY0059' was accomplished when vegetative stem cuttings were propagated from the initial selection in June 2018 in a controlled environment in Enkhuizen, The Netherlands.

BRIEF SUMMARY OF INVENTION

Horticultural examination of plants grown from cuttings of the plant initiated in June 2018 and continuing thereafter, has demonstrated that the combination of characteristics as herein disclosed for 'PEHY0059' are firmly fixed and are retained through successive generations of asexual reproduction.

'PEHY0059' has not been observed under all possible environmental conditions. The phenotype may vary significantly with variations in environment such as temperature, light intensity, and day length.

A Plant Breeder's Right for this cultivar was applied for in the European Union on Jul. 16, 2021, No. 2021/1877. 'PEHY0059' has not been made publicly available prior to the effective filing date of this application, notwithstanding any disclosure that may have been made less than one year prior to the effective filing date of this application by the inventor or another who obtained 'PEHY0059' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0059' with colors being as true as possible with an illustration of this type.

Figure 1:
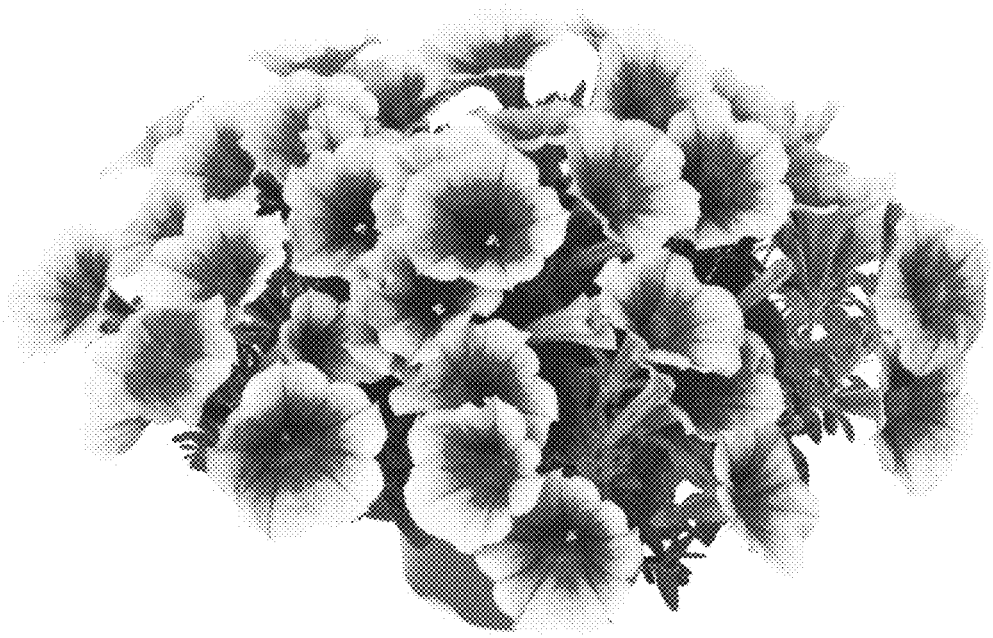
Figure 2:
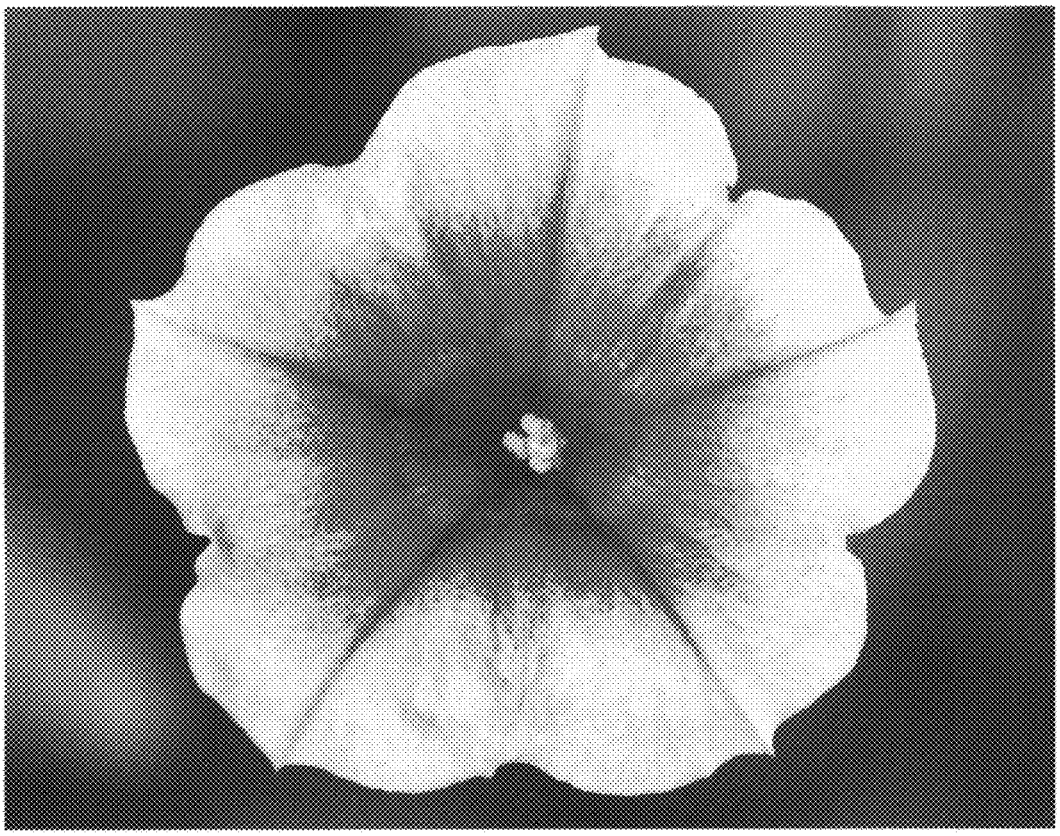

The photographic drawings show in FIG. 1 a flowering plant of the new variety and in FIG. 2 a close-up of the flowers.

DETAILED BOTANICAL DESCRIPTION

The aforementioned photographs were taken in May 2020 from plants growing indoor in 12 cm pots in Andijk, The Netherlands. These plants were approximately 12 weeks of age.

The plant descriptions and measurements were taken in September 2021 in Enkhuizen, The Netherlands on approximately 12 week old plants that were growing in containers.

Color references are made to The Royal Horticultural Society Colour Chart (RHS) 2001.

TABLE 1

DIFFERENCES BETWEEN THE NEW VARIETY 'PEHY0059' AND A SIMILAR VARIETY

| | PEHY0059' | 'Aurora Banana Candy' (not patented) |
|---|---|---|
| Flower color pattern: | Rather big colored eye of flower | Small colored eye |
| Flower colour stability: | Yellow color of young flower fading into soft yellow | Stable yellow flower color |
| Flower size: | Small to medium size | Medium size |

Plant:

*Form, growth and habit.*—Mounding to spreading plant habit.

*Plant height.*—20 cm.

*Plant height (inflorescence included).*—23 cm.

*Plant diameter (width).*—Approximately 29 cm.

Roots:

*Number of days to initiate and produce roots.*—16 days at about 22° C.

*Type.*—Fine, fibrous, free branching.

*Color.*—RHS N155D.

Foliage:

*Arrangement.*—Alternate, simple; sometimes opposite, decussate.

*Immature leaf, color upper surface.*—RHS 137C.

*Immature leaf, color lower surface.*—RHS 137D.

*Mature leaf, color upper surface.*—RHS 137A.

*Mature leaf, color lower surface.*—RHS 137B.

*Length.*—2-3.5 cm.

*Width.*—1.5-2.0 cm.

*Shape.*—Ovate.

*Base shape.*—Shortly Attenuate.

*Apex shape.*—Acute.

*Margin.*—Entire.

*Texture, upper surface.*—Densely covered with short hair.

*Lower surface.*—Densely covered with short hairs.

*Color of veins, upper surface.*—RHS 137C.

*Color of veins, lower surface.*—RHS 137C.

*Petiole color.*—RHS 137C.

*Length.*—0.2 cm.

*Diameter.*—0.2 cm.

*Petiole texture.*—Densely covered with short hairs.

Stem:

*Quantity of main branches per plant.*—4-5.

*Color of stem.*—RHS 137C.

*Length of stem.*—17 cm.

*Diameter.*—0.3 cm.

*Length of internodes.*—2.0-3.0 cm.

*Texture.*—Dense, mostly glandular short hairs.

*Color of pedicel.*—RHS 137C.

*Length of pedicel.*—1.8 cm.

*Diameter of pedicel.*—0.2 cm.

*Texture of pedicel.*—Densely covered with short hairs.

Inflorescence:

*Type.*—Flowers solitary in upper leaf axis.

*Floret type.*—Funnel-shaped; 5 lobed petals; fused at base.

*Blooming habit.*—Medium early flowering in greenhouse, flowering throughout the summer months.

*Quantity of inflorescences per plant.*—Approximately 45.

*Lastingness of individual blooms on the plant.*—About 7 days.

*Fragrance.*—Rather strong smell.

Bud (just when opening):

*Color.*—RHS 154A at top, 152B towards base.

*Length.*—3.2 cm.

*Width.*—0.6 cm.

*Shape.*—Oblong.

Immature inflorescence:

*Flower horizontal diameter.*—3.7 cm.

*Color petals, upper surface.*—RHS 7A, with centre of flower RHS 53B.

*Color petals, lower surface.*—RHS 154C, with a hue of RHS 152C towards tube.

Mature flower:

*Flower horizontal diameter.*—4.7 cm.

*Flower height (vertical).*—2.8-3.2 cm.

*Color upper surface.*—RHS 3C, fading into RHS 3D at moment of senescense, with centre of flower RHS 61C, turning into RHS 64B at moment of senescense.

*Color lower surface.*—RHS 145C, with a hue of RHS 152C.

*Conspicuousness of veins.*—Medium, but rather strong on lower surface.

*Apex shape.*—Acuminate.

*Margin.*—Entire.

*Waviness of margin.*—Medium.

*Petal lobation.*—Medium.

*Petal texture, upper surface.*—Smooth.

*Petal texture, lower surface.*—Smooth, occasionally a short hair.

*Corolla tube color outside.*—RHS 60B with veins 142A.

*Corolla tube color inside.*—RHS 178C.

*Conspicuousness of veins in tube.*—Medium to low.

*Corolla tube length.*—2 cm.

*Corolla tube texture, outside.*—Rather dense and short glandular hairs.

*Corolla tube texture, inside.*—Glabrous.

Calyx:

*Color of sepal, upper surface.*—RHS 137C.

*Color of sepal, lower surface.*—RHS 137D.

*Length.*—1.4 cm.

*Width.*—0.3 cm.

*Shape.*—Ensiform.

*Apex shape.*—Acute.

*Base.*—Fused.

*Margins.*—Entire.

*Texture, upper surface.*—Densely covered with short glandular hairs.

*Lower surface.*—Densely covered with short glandular hairs.

Reproductive organs:

*Pistil.*—1.

*Length.*—2.2 cm.

*Style color.*—RHS 145D.

*Style length.*—1.5 cm.

*Stigma color.*—RHS 142D.

*Stamens.*—

*Quantity per flower.*—5.

*Color of filaments.*—RHS 192D.

*Length filaments.*—1.3 cm.

*Anther color.*—RHS 157A.

*Anther length.*—0.2 cm.

*Anther shape.*—Elliptical.

*Color of pollen.*—RHS 155B.

*Pollen amount.*—Sparse.

*Fertility/seed set.*—Has not been observed on this hybrid.

*Disease/pest resistance.*—Has not been observed on this hybrid.

What is claimed is:

1. A new and distinct variety of *Petunia* plant named 'PEHY0059' substantially as illustrated and described herein.

* * * * *